(12) United States Patent
Carroll (10) Patent No.: US 11,419,403 B2
(45) Date of Patent: Aug. 23, 2022

(54) SANITIZING AND CLEANING SYSTEM FOR FINGERS

(71) Applicant: Geoffrey Porter Carroll, Maitland, FL (US)

(72) Inventor: Geoffrey Porter Carroll, Maitland, FL (US)

(*) Notice: Subject to any disclaimer, the term of this patent is extended or adjusted under 35 U.S.C. 154(b) by 0 days.

(21) Appl. No.: 15/168,515

(22) Filed: May 31, 2016

(65) Prior Publication Data
US 2016/0345707 A1    Dec. 1, 2016

Related U.S. Application Data

(60) Provisional application No. 62/167,407, filed on May 28, 2015, provisional application No. 62/198,294, filed on Jul. 29, 2015.

(51) Int. Cl.
| | |
|---|---|
| *A45D 29/17* | (2006.01) |
| *A46B 9/02* | (2006.01) |
| *A46B 11/00* | (2006.01) |
| *A61L 2/00* | (2006.01) |
| *A45D 29/00* | (2006.01) |
| *B08B 1/00* | (2006.01) |

(52) U.S. Cl.
CPC ......... *A45D 29/17* (2013.01); *A45D 29/007* (2013.01); *A46B 9/021* (2013.01); *A46B 11/00* (2013.01); *A61L 2/0088* (2013.01); *A46B 2200/1013* (2013.01); *B08B 1/002* (2013.01)

(58) Field of Classification Search
CPC ...... A45D 29/17; A45D 29/007; A46B 9/021; A46B 11/00; A46B 9/02; A61L 2/0088; B08B 1/002
See application file for complete search history.

(56) References Cited

U.S. PATENT DOCUMENTS

| | | | | | |
|---|---|---|---|---|---|
| 1,943,225 | A | * | 1/1934 | McIntyre | A46B 9/04 15/167.1 |
| 2,580,981 | A | * | 1/1952 | Webster | A45D 29/00 132/73 |
| 3,281,881 | A | * | 11/1966 | Yetter | A45D 29/17 15/104.92 |
| 3,966,335 | A | * | 6/1976 | Abramson | A46B 9/02 401/10 |
| D242,668 | S | * | 12/1976 | Kaufman | D4/120 |
| 4,644,966 | A | * | 2/1987 | Ferrari | A45D 29/007 132/73 |
| 4,671,306 | A | * | 6/1987 | Spector | A45D 29/007 132/73 |
| 4,819,672 | A | * | 4/1989 | Walker | A45D 29/007 132/73.5 |

(Continued)

*Primary Examiner* — Joseph L. Perrin
*Assistant Examiner* — Kevin G Lee
(74) *Attorney, Agent, or Firm* — Accel IP Law, PLLC; Ferdinand (Fred) M. Romano (57) ABSTRACT

Systems and methods for cleaning or sanitizing a finger. A container has an interior sized to receive a finger, the container having a bottom portion and a wall portion extending from the bottom portion to an opening along an edge of the wall portion through which the finger may be received. The wall portion and bottom portion each have an interior surface within the container. A plurality of bristles extend from an interior surface of the container for contact with a portion of the finger when liquid is in the container.

21 Claims, 6 Drawing Sheets

(56) References Cited

U.S. PATENT DOCUMENTS

| | | | | |
|---|---|---|---|---|
| 4,866,806 A * | 9/1989 | Bedford | ............ | A47L 13/16 |
| | | | | 15/104.94 |
| 5,379,474 A * | 1/1995 | Nakamura | ............ | A46B 9/02 |
| | | | | 132/73.6 |
| 5,806,536 A * | 9/1998 | Tietjen | ............ | A45D 31/00 |
| | | | | 132/73 |
| 6,290,418 B1 * | 9/2001 | Frey | ............ | A45D 40/0075 |
| | | | | 401/126 |
| 7,500,282 B1 * | 3/2009 | Park | ............ | A47K 7/02 |
| | | | | 15/160 |
| 7,918,233 B2 * | 4/2011 | Burgess | ............ | A45D 29/04 |
| | | | | 132/75.6 |
| 8,999,907 B2 * | 4/2015 | Datta | ............ | C08L 23/08 |
| | | | | 508/591 |
| 2003/0226570 A1 * | 12/2003 | Kurokawa | ............ | A45D 29/007 |
| | | | | 132/73 |
| 2015/0289636 A1 * | 10/2015 | Myers | ............ | A46B 15/0028 |
| | | | | 15/22.1 |

* cited by examiner

SANITIZING AND CLEANING SYSTEM FOR FINGERS

RELATED APPLICATIONS

This application claims priority to U.S. Provisional Patent application Ser. No. 62/167,407 filed May 28, 2015 and U.S. Provisional Patent application Ser. No. 62/198,294 filed Jul. 29, 2015. This application is related to PCT/US15/64631 filed Dec. 9, 2015 which is incorporated herein by reference.

FIELD

The present invention concerns cleaning and sanitizing and, more specifically, relates to systems and methods that provide fast and convenient cleaning or sanitizing of fingers, including fingernails.

BACKGROUND

As application PCT/US15/64631 notes, in recent years there has been an increased social expectation to limit communication of diseases through use of gloves, washing of hands and use of hand sanitizing liquids. These are prevalent in many interactions which might expose persons to contagious diseases. Although concerns about the spread of infection clearly extend beyond occupational activities, it is widely recognized that contact with persons providing health care and food handling services can be a major pathway to the spread of disease. Even casual hand contact with the skin or clothing of another person may lead to deposit of infectious material in crevices along the fingers that could pose health risks.

While it is recognized that application of sanitizing liquids on the surface of the hands can have a germicidal effect, simple rubbing of a sanitizing liquid on the hands is not a totally effective means for removing bacteria from crevice regions of the same hands. Liquid sanitizers require time to apply the liquid, complete the sanitizing process and sometimes remove residual material. There has not been a fast and convenient way of sanitizing portions of the hands which contain significant crevices. Because these areas do not readily or reliably receive the beneficial effects resulting from the simple rub-on application of sanitizing liquid to the skin, they are more prone to collect debris and provide moist environments to sustain bacterial growth.

Also, existing application methods do not assure deep penetration of the liquid into regions such as crevices along fingernails, to guarantee that the sanitizing liquid is one hundred percent effective.

There is a need for a portable system which is quick and easy to utilize for thorough cleaning or sanitizing of the fingers, including fingernails. The ideal system will reduce infections and the spread of germs. The system may be reusable, but disposable embodiments of the system can further assure isolation of contagious pathogens.

SUMMARY OF THE INVENTION

In one series of embodiment a system is provided for cleaning or sanitizing a finger or a region about a fingernail. A container for holding liquid, has an interior sized to receive a finger. The container has a bottom portion and a wall portion for containing liquid. The wall portion extends from the bottom portion to an opening along an edge of the wall portion through which opening a finger may be received into the container. The wall portion has opposing exterior and interior wall surfaces. A majority or the entirety of the interior wall surface extends along the exterior surface. The bottom portion has opposing exterior and interior bottom surfaces. The interior bottom surface faces the container interior. The container includes a plurality of bristles extending from one or both interior surfaces of the container for contact with a portion of a finger inserted in the container. The system may include a removable lid positioned against the edge of the wall portion to seal the opening and keep liquid placed in the container prior to use of the system for cleaning or sanitizing. The heights of bristles may vary considerably. An exemplary range applicable to the illustrated patterns is from about 3 mm to 1 cm. The widths or diameters of the bristles may vary from 0.08 mm to 0.16 mm. The bristles have an elongate height relative to bristle width or diameter. The ratio of height to width or height to diameter may, for example, range from less than 37 to more than 125. Bristles of differing heights and widths (or diameters) may be mixed in patterns and multiple patterns of bristles may be formed along the interior wall and bottom surfaces, e.g., to provide a user with a variety of bristle cleaning surfaces.

In another series of embodiments, a system is provided for cleaning or sanitizing a finger or a region about a fingernail, including a container for holding liquid, the container having an interior sized to receive a finger. The container has a bottom portion and a wall portion for containing liquid. The wall portion extends from the bottom portion to an opening along an edge of the wall portion through which a finger may be received into the container. The container has an upper interior surface along the wall portion and a lower interior surface along the bottom portion. The container includes a first group of bristles extending upward from the lower interior surface toward the container opening for contact with a portion of a finger positioned within the container. The container may further include a second group of bristles extending from the upper interior surface for contact with a portion of a finger. The container may be axially symmetric between the bottom portion and the opening with bristles in the second group extending from the upper interior surface toward a central axis of symmetry. The edge of the wall portion may be a sealing lip, with the system including a removable seal lid bonded to the sealing lip to keep liquid placed in the container prior to use of the system for cleaning or sanitizing. The bond between the seal lid and the sealing lip may be effected with application of an adhesive, a heating process, or welding.

In another series of embodiments a method is provided for cleaning or sanitizing fingers, including positioning a finger along an interior surface of a container filled with fluid. A portion of the finger is moved along a series of varying bristle patterns immersed in the fluid to clean or sanitize the finger portion with the fluid. The step of moving a portion of the finger may be performed with bristles mounted along a bottom surface of the container.

In still another series of embodiments a method for cleaning or sanitizing fingers with a portable container includes providing a sealed, portable container holding a liquid suitable for sanitizing or cleaning fingers. A seal is peeled off an opening of the container to expose an interior surface containing one or more patterns of bristles. A finger is inserted through the opening to contact a portion of the bristles. A portion of the finger is rubbed against the bristles to clean or sanitize a region about a finger nail or other portion of the finger. The finger may contact bristles along a bottom surface in the container to clean or sanitize a fingertip. The method may include sequentially inserting multiple fingers through the opening for cleaning or sanitizing with a rubbing action along the bristles.

BRIEF DESCRIPTION OF THE FIGURES

The following drawings are provided to facilitate understanding of concepts and designs presented in the written description which follows, where.

Like reference numbers are used throughout the figures to denote like components. Components may be schematically illustrated, and various details, connections and components of an apparent nature may not be shown in order to emphasize details of other components. Orientations of the disposable system are shown with respect to a horizontal ground plane. Orientations of components of the system are at times described with reference to vertical and horizontal orthogonal directions, where vertical directions are parallel to a vertical axis of the illustrated container. Various features shown in the figures are not drawn to scale.

DETAILED DESCRIPTION OF THE INVENTION

Embodiments of the invention incorporate bristles, generally understood to mean projections suitable for scrubbing or cleaning along a surface. The term bristle generally refers to such a structure extending away from a surface, having an elongate height relative to a bristle width or diameter. Bristle height refers to the dimension measurable along a direction in which the bristle extends away from the surface to which a first end is fixed. The bristle terminates at a second end, opposing the first end, positioned for making cleaning contact with a surface of a finger. Being elongate, the bristle height is relatively large compared to a width dimension or diameter of the bristle. In this context of cleaning with a scrubbing or agitating action, bristle refers to any flexible and resilient structure that can perform such a function, and is not at all limited to conventional shapes or materials. For example, bristles incorporated in embodiments of the invention may have cylindrically shaped walls and flat ends for cleaning or scrubbing contact. These and other elongate shapes may also taper (e.g., to be pointed or rounded) at the second end which makes contact with a surface for cleaning, to facilitate making contact within small grooves or other features along the surface of a finger. It is well known to fabricate bristles of nylon (e.g., for toothbrushes) and other polymers (e.g., for hair brushes). Choices of size, shape and material may be based on a desired type of cleaning action. Depending on whether the desired cleaning action is to be relatively hard or soft, bristles could be made relatively stiff or supple (e.g., resilient) so as not to have a harsh or irritating effect on the skin surface.

In numerous embodiments of the cleaning system, a series of spaced apart bristles is arranged in an array of rows and columns or concentric shapes. Bristle height, width or diameter, shape or composition may vary from row to row to provide preferred combinations of features. Exemplary spacings between adjacent bristles in an array may vary with the width or diameter of the bristles. For an exemplary bristle diameter ranging from about 0.08 mm (1/32 in) to 0.16 mm (1/16 in), the spacings between bristles may range from 0.2 mm to 0.3 mm.

Figure 1:
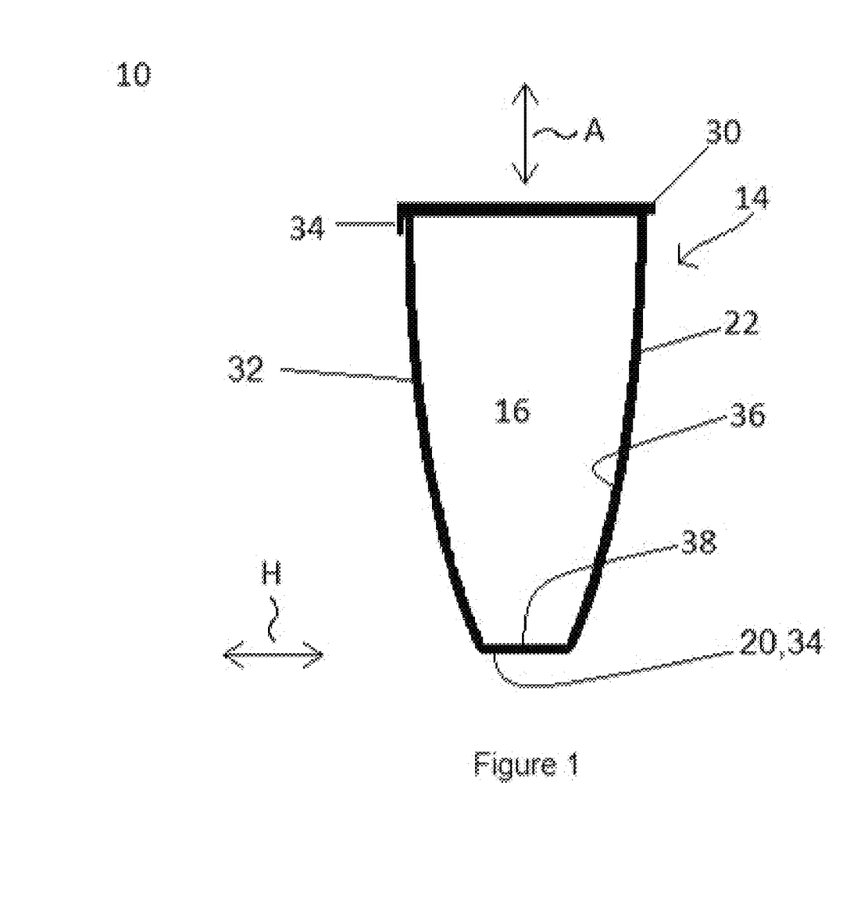
FIG. 1 provides an elevation view of a disposable system for nail and finger sanitizing or cleaning according to an embodiment of the invention.

FIG. 1 provides an elevation view of a disposable system 10 for nail and finger sanitizing or cleaning according to one embodiment. The system comprises a sealed container 14 which holds a quantity of sanitizing and/or cleaning liquid 16 for application on demand. The term liquid as used herein includes any kind of liquid generally, including gels, and specifically includes liquids having cleaning properties (e.g., solvents), moisturizers, materials having disinfecting or antiseptic properties and other fluids.

The container 14 includes a bottom 20 and a wall 22 which extends upward from the bottom along a vertical axis, A, with respect to a horizontal ground plane, H, to an opening 24. The opening is bounded by a rim, referred to as a sealing lip 26, along an edge 28 of the wall 22. See, also, FIG. 2. A seal lid 30, shown in FIG. 1, is bonded to the sealing lip 26 to form a closed vessel with the container 14 and prevent loss of liquid 16 placed therein when the axis is not vertical with respect to the horizontal ground plane. The bond between the seal lid 30 and the sealing lip 26 may be effected with application of an adhesive, pressure, via a heating process, by welding, or with another well-known technique.

The container 14, having an exemplary tapered shape along the vertical axis, may be sized for convenience and portability. For example, the container may have an overall container height of 5 to 6 cm and an outside diameter of 2.5 to 3 cm about the sealing lip 26. The exemplary height is based on sanitizing or cleaning only the portion of a finger extending from the fingertip to the second joint in the longest finger of a user, but in other embodiments, the container height may be sized to receive substantially the entire length of a finger, e.g., 9 to 12 cm. As shown for the illustrated embodiment, the outside diameter of the container may diminish from the selected maximum outside diameter (providing a relatively wide opening near the sealing lip) to a minimum diameter near the bottom 20, with the interior diameter diminishing from the sealing lip 26 to the bottom 20 by, for example, 0.5 to 1 cm. In other embodiments, a series of containers may be provided for multiple systems where the sizes of the containers vary based on finger size (e.g., length, width, or circumference about the finger), in a manner analogous to the way numerous glove sizes provide appropriate fits for hands of differing dimensions, and so a user can avoid having to carry a larger size system 10 than is needed. The illustrated shape of the container 14 is shown to be symmetrical about the axis, A, (e.g., a modification to a straight cylindrical body where the radius from the central axis varies as a function of position along the axis). The container may have any of numerous other functional or artistic shapes without departing from the spirit of the invention.

The seal lid 30 is a relatively thin flexible layer (e.g., in the range of 30 to 50 microns) serving as a moisture impervious membrane. The seal lid material may comprise a metallic foil (e.g., aluminum), a polymer sheet or a cellulose product such as a coated paper or a cellophane product. With the seal lid 30 bonded to the sealing lip 26 of the container 14, the liquid 16 remains in the container until use of the system 10 is initiated by, for example, peeling of the seal lid 30 away from the sealing lip 26 or breaking of the seal lid by penetration. The seal lid 30 may be designed to be penetrated by application of a force with the tip of a finger. The seal lid may, as shown in the figures, have a pull tab 34 for removal. Once the seal lid is broken or removed, a user may dip a portion of a finger into the container 14 to immerse the finger portion into the liquid 16.

The container has an exterior wall surface 32 and an exterior bottom surface 33, each facing away from the container, an interior wall surface 36 and an interior bottom surface 38. The majority or entirety of the interior wall surface 36 follows the contour of the exterior wall surface 32. The interior bottom surface 38 may be substantially parallel with the bottom surface or may be contoured to receive the shape of the tip of a finger.

Figure 2:
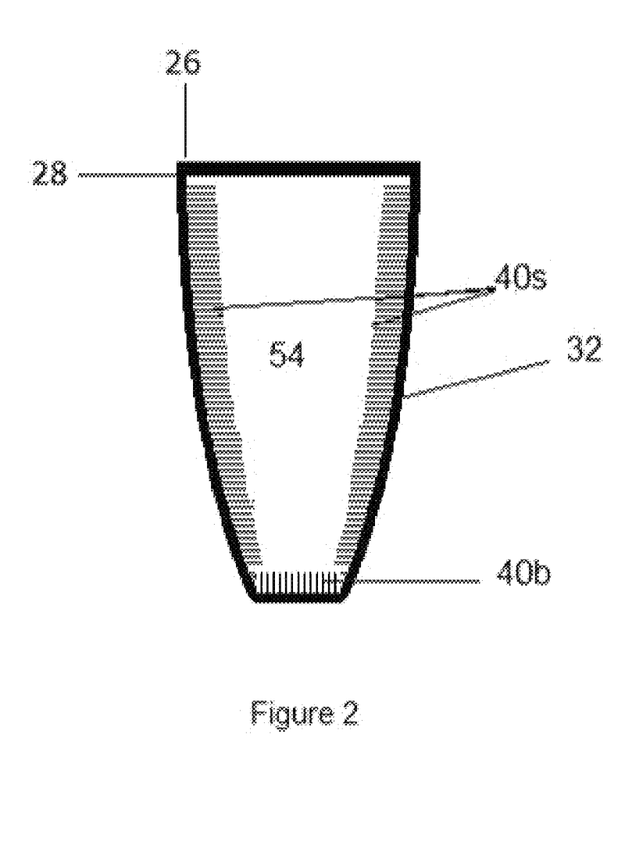
FIG. 2 is a partial view in cross section of a container of the disposable system shown in FIG. 1 illustrating features along an interior wall surface and an interior bottom surface of the container.
Figure 3A:
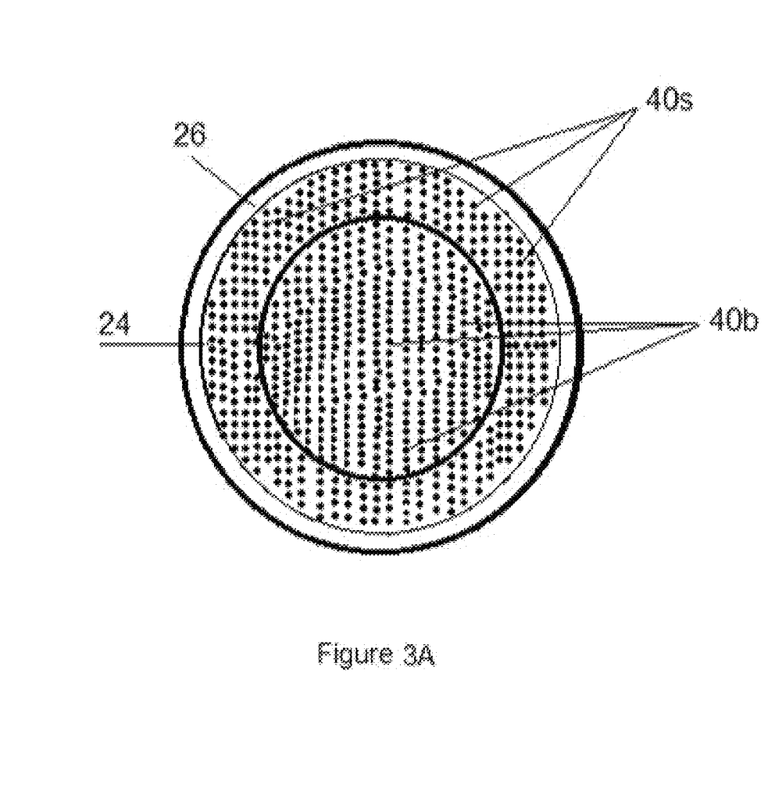
FIG. 3A is a plan view of the container shown in FIG. 2.
Figure 3B:
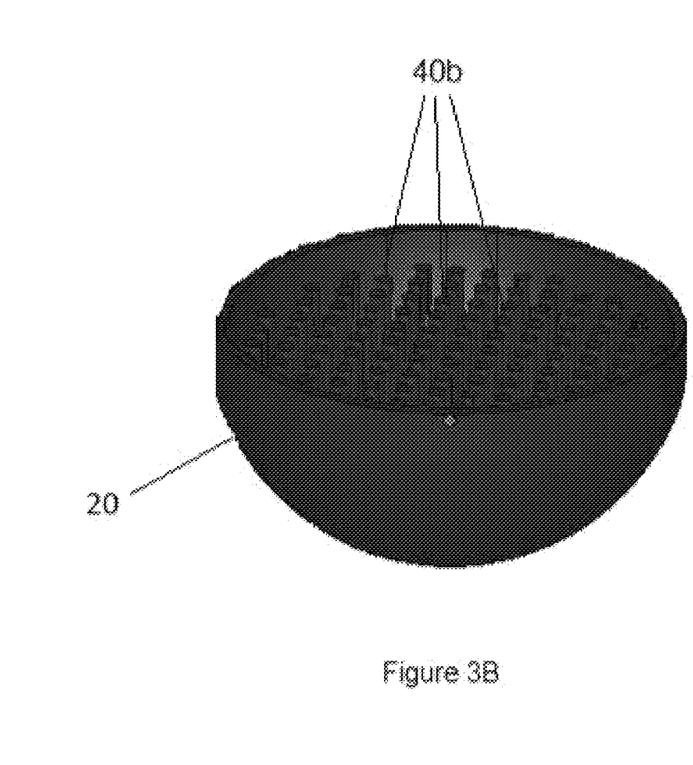
FIG. 3B is a perspective view of a portion of the container shown in FIGS. 2 and 3A, illustrating a series of bristles formed in an exemplary pattern along an interior bottom surface of the container.
Figure 4:
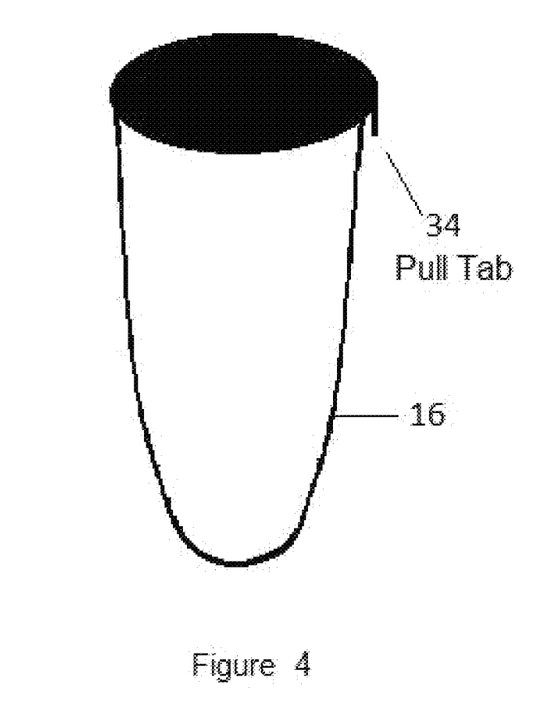
FIG. 4 is a perspective view of the container with an opaque seal lid positioned over an opening of the container.

FIG. 2 is a partial view of the container 14 with the seal lid removed. The view is taken along a plane which resides in the axis, A, to illustrate features along the interior wall surface 36 and the interior bottom surface 38 of the container. Brush-like members, generally referred to herein as bristles 40 extend from the interior surfaces 36, 38. Exemplary patterns of the bristles are shown in FIGS. 2, 6, 7 and 8. A series of side bristles 40s extend from portions of the interior wall surface 36 toward diametrically opposite portions of the interior wall surface. In one series of embodiments, the bristles may extend toward the axis, A. A series of bottom bristles 40b extend from the interior bottom surface 38 toward the opening 24. FIG. 3A is a view of the container 14 with the seal lid absent. The view is taken from above the sealing lip 26 and along the axis, A, to further illustrate exemplary patterns of the side and bottom bristles 40s, 40b. FIG. 3B provides further views of the bottom bristles 40b, illustrating an exemplary pattern having vertical bristles 40b arranged in uniform rows and columns perpendicular to one another along the interior bottom surface. The bristles 40s formed along the interior wall surface 36 may be similar in size and shape to the bristles 40b shown along the interior bottom surface 38. FIG. 4 provides a perspective view of the container 14 with an opaque seal lid 30 (e.g., formed with a layer of aluminum foil) bonded to the sealing lip 26.

Referring again to FIG. 2, side bristles 40s, positioned along the inner surface 36 of the container wall 22, are sized to provide for scrubbing of the nail plate including the lunula, the cuticle, the nail fold and other portions of the finger with the liquid. Bottom bristles 40b positioned along the interior bottom surface 38 are sized to facilitate scrubbing the hyponychium and, generally, regions of the fingernail adjoining the fingertip.

Figure 6:
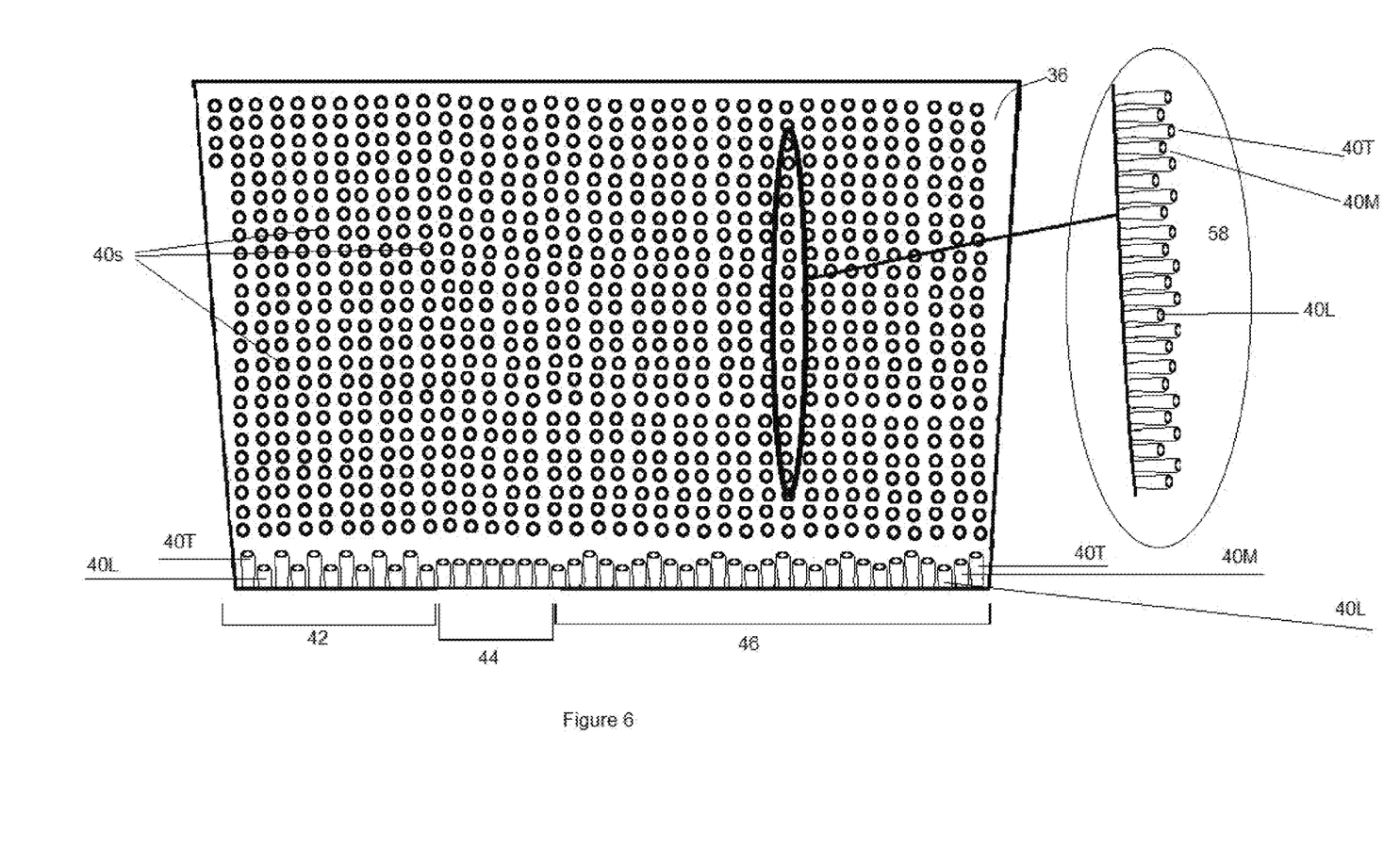
FIG. 6 is an unrolled view of a series of side bristles arranged in row and columns and further illustrates exemplary bristle patterns in a side view of the bristles.
Figure 7:
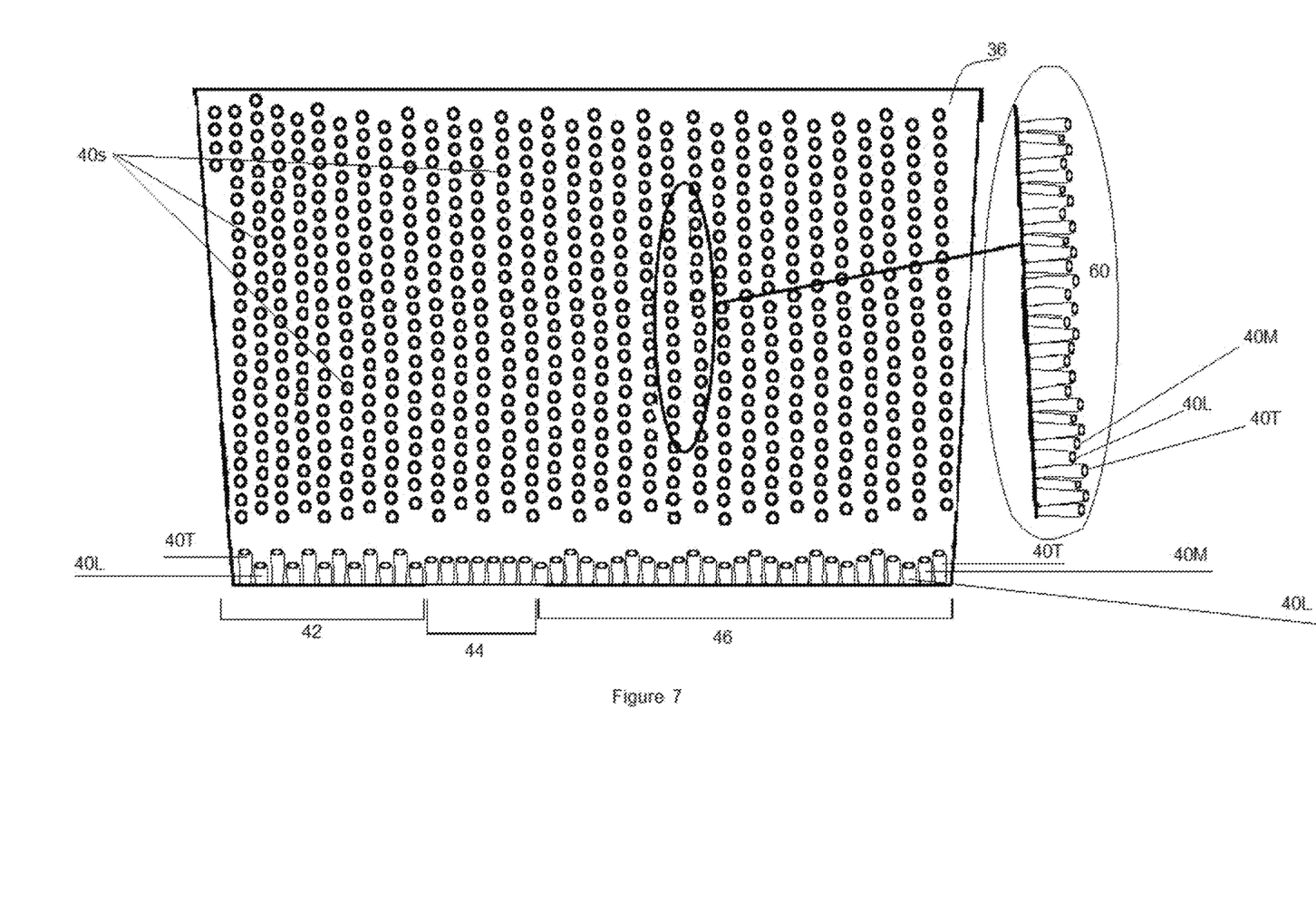
FIG. 7 is an unrolled view of a series of side bristles arranged in rows and alternately staggered columns along a vertical direction and further illustrates exemplary bristle patterns in a side view of the bristles for this arrangement.
Figure 8:
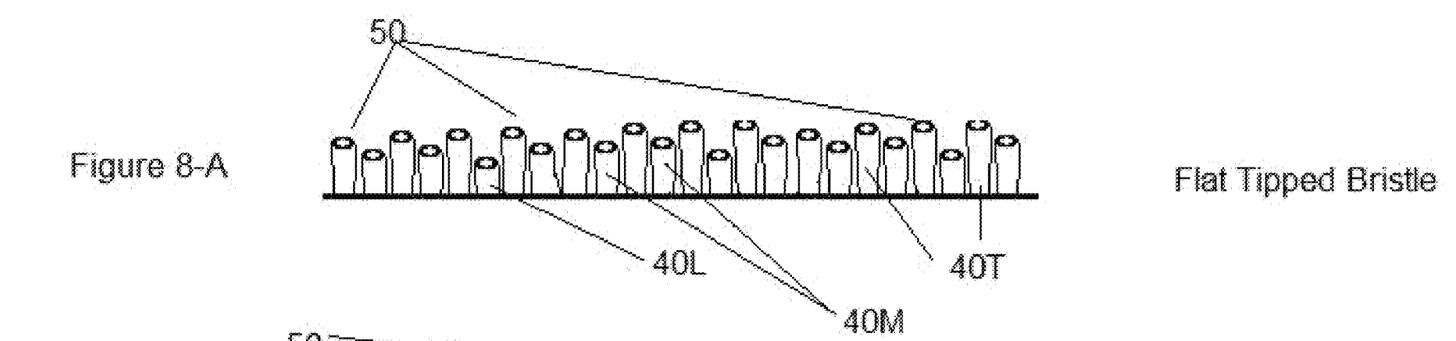
FIGS. 8A through 8C are side views of bristle patterns illustrating exemplary profiles for three shapes of bristle ends.

FIGS. 6 and 7 provide unrolled interior views of the container shown in FIG. 2. The unrolled view of FIG. 6 illustrates a series of side bristles 40s arranged in row and columns along the interior wall surface 36. The lower portion of FIG. 6 also illustrates a side view of three series of bristles to illustrate exemplary bristle patterns 42, 44, 46 based on exemplary bristle height variations from row to row or from column to column in the array. The illustration aligns individual bristles with vertical columns, but the patterns also apply to bristles along different horizontal rows in each matrix of row and columns. The inset view 58 of FIG. 6 provides a side view of bristles 40s along a column, again illustrating the alternating bristle height pattern 44 for bristles along a vertical column.

The exemplary bristle shapes and patterns 42, 44, 46 shown in the figures for side bristles 40s are also exemplary of bristle shapes and patterns for bottom bristles 40b. The example patterns 42, 44, 46 illustrate bristles of three height variations: low height bristles 40L, medium height bristles 40M and tall height bristles 40T. The first pattern 42 is an alternating sequence of bristles 40T and 40L. The second pattern 44 is a uniform sequence of bristles having the same height 40M. The third pattern is a sequence having a saw tooth arrangement with bristle height varying as 40L, 40M, 40T, 40M, 40L, 40M, 40T, 40M, etc. FIG. 7 illustrates an array pattern of rows and columns in which bristles in adjacent columns are staggered with respect to one another in the vertical direction. The inset view 60 of FIG. 7 provides a side view of bristles in two adjacent columns, with bristles in the same column following the first pattern 42 of bristle heights.

FIGS. 8A through 8C are side views of three series of bristle patterns illustrating profiles for three exemplary shapes of bristle ends 50 which come into contact with finger surfaces. The ends 50 of cylindrically shaped bristles shown in FIG. 8A are flat. The ends 50 of bristles shown in FIG. 8B are pointed, and the ends 50 of bristles shown in FIG. 8C are rounded.

Generally, groups of bristles may be formed in patterns where bristle features, such as height, width and stiffness, vary from pattern to pattern or from bristle to bristle in rows or columns. These patterns provide for a variety of scrubbing characteristics or enable simultaneous contact by bristles against adjoining surfaces of contours, e.g., portions of finger surfaces having crevices or grooves.

Figure 5:
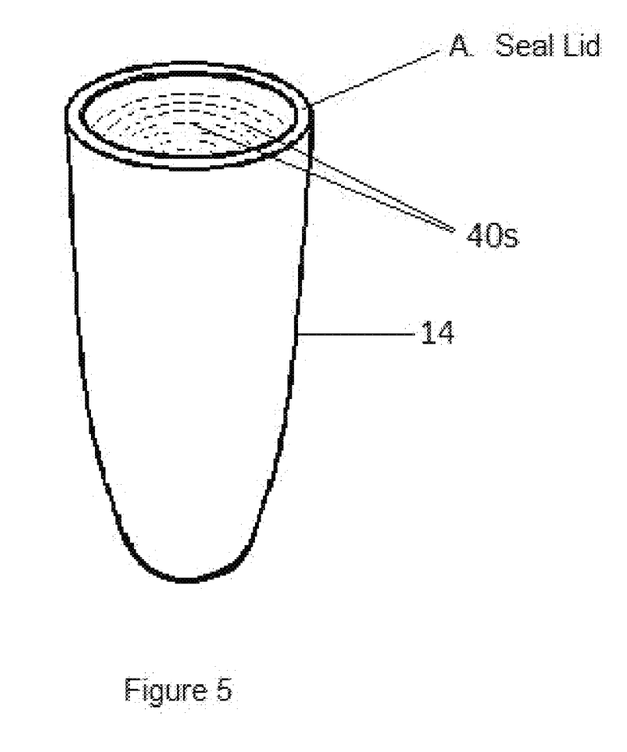
FIG. 5 is a perspective view of the container showing side bristles along an interior wall surface of the container.

The exemplary container 14 shown in the figures is in the shape of a cup having radial symmetry about the vertical axis, A. FIG. 5 is a perspective view of the container 14 at an angle of about 25 degrees with respect to the vertical axis, A, showing side bristles 40s along the interior wall surface 36 of the container.

FIG. 6 is another partial perspective view of the container 14 taken along the axis, A, illustrating rows of bottom bristles 40b having an exemplary cylindrical bristle shapes. The container bottom surface 38 may be flat, convex or concave as to provide greater effectiveness when imparting a rocking or scrubbing motion for a part of a finger, e.g., a fingernail. The container shape may also be optimized for convenience of storage (e.g., in a pocket), packing and shipping. The bristles 40s, 40b may be made of different materials (e.g., a thermo plastic, such as a nylon used for bristles of a toothbrush) or plastic used in an integrated molding process (which forms the bristles as part of the container wall or bottom). The bristles 40 may be formed of other materials (e.g., natural fibers and metals). The bristles 40 may be formed in discrete layers, each layer being a portion of an interior surface 36 or 38 of the container 14, each layer containing an array of bristles. The bristles may be formed as discrete members, each applied to an interior surface to form one or more patterns after the wall 22 or bottom 20 is formed. In other embodiments, patterns of bristles may include bristles of varied size to better effect scrubbing. For example, the height in a series of bristles (relative to the interior surface from which the bristles extend) may vary from relatively short to relatively tall heights (e.g., to 0.5 mm in height along the interior wall surface 36 and to 1.0 mm in height along the interior bottom surface 38). For a given height, the bristles may have a variety of lengths and widths or diameters. The terms length, width and diameter as applied to a bristle 40 refer to dimensions in directions perpendicular to the direction along which the bristle height is measured, or along a direction of the interior surface from which the bristle extends. The lengths, widths or diameters of the bristles may, for example, range from 0.1 mm to 1.0 mm and may be of cylindrical shapes as shown in FIGS. 3B and 6. Moreover, the lengths in a series of bristles may vary monotonically from relatively short to relatively long as a function of position along the interior surfaces 36, 38 of the wall 22 or the bottom 20, so the user may select a region along a surface having optimal bristle characteristics (e.g., stiffness, height, diameter, etc.) for scrubbing a particular region of the finger. In other embodiments the bristle length may vary so that bristles of different heights are mixed in a continual pattern to allow short and long bristles to simultaneously contact surface contours created by adjoining regions.

I have described a disposable fingernail and finger sanitizing and cleaning system which enables a rapid, easily utilized method of cleaning and sanitizing beneath fingernails and along portions of fingers. An embodiment of the related method includes opening the container by piercing or removing the seal lid, penetrating a finger into a liquid contained therein and scrubbing the finger parts against bristles formed along inner surfaces of the container. In other embodiments a re-usable fingernail and finger sanitizing and cleaning system is provided. The re-usable system comprises a lid seal in the form of a cap or a stopper. In lieu of bonding a lid seal to a sealing lip 26, a flip cap may be attached at a hinge point to the container to selectively expose the opening for extension of a finger into liquid within the container. There may be a seal at the interface between the cap and the sealing lip 26 to prevent leakage of cleaning or sanitizing liquid from the container.

A feature of the disclosed embodiments is provision of a container comprising bristles along an interior wall surface and an interior bottom surface where the bristles 40s along the wall surface extend only a limited distance toward the axis, A. This leaves an open region 54 along the axis, A. The region 54 may be of variable width as shown in FIG. 2, between ends 50 of opposing wall bristles. For example, with the height of the container 14, as measured along the axis, A, ranging between 4.5 cm and 7 cm, the container opening 24 may range between 2.5 cm and 3 cm, a maximum width of the region 54. A minimum width of the region 54, along the interior bottom surface 38, corresponds to the area occupied by the bottom bristles 40b, e.g., a circular region having a diameter of about 2.6 cm or one inch. For the illustrated embodiment, the minimum width (or diameter) of the region 54 along the area occupied by the bottom bristles is the diameter of the circular area. This area occupied by the bottom bristles is sufficiently large to permit lateral movement of a fingertip along the bottom bristles for effective scrubbing movement against the bristles 40b. The array of bristles 40b shown in FIG. 3A may have other shapes such as, for example, a square pattern having side dimensions of 2.6 cm. The invention provides personnel with a disposable and portable method of sanitizing and cleaning fingers and nails to aid in cleanliness, skin treatment (e.g., moisturizing), and reducing healthcare-related spread of infections such as MRSA (Methicillin-Resistant *Staphylococcus Aureus*). The invention is generally useful to advance sanitary conditions by cleaning or sanitizing regions beneath a person's fingernails and other regions of the fingers. The illustrated embodiment of a disposable Nail and Finger Sanitizer and Cleaner may also be used for industrial and commercial environments, including the food service industry and in households or living quarters for normal cleaning and sanitary use. The system is especially useful for medical staff and can benefit young children for which nail file tips are painful and possibly detrimental to fingernails.

I claim:

1. A portable system, for sanitizing fingers of a human hand including finger tips, nails and joints, with each finger extending into the system at least from the fingertip to both a first finger joint and a second finger joint, including regions about a finger nail, the system comprising:
    a sealed container and a sanitizing liquid stored therein, the container having an interior sized to receive individual fingers, a bottom portion and a wall portion for containing liquid, the wall portion extending along a central axis of the container a height from the bottom portion to an opening along an edge of the wall portion through which each of the fingers can be received into the container, the height of the container sufficient to enable the first finger to extend into the container from the finger tip to at least the second finger joint,
    the container having an upper surface along the wall portion and a lower surface along the bottom portion, the container further comprising:
    a first group of bristles extending upward from the lower surface toward the container opening for contact with a first portion of the finger when a part of the finger is positioned within the container;
    a second group of bristles extending inward from the upper surface along the wall portion for contact with a second portion of the finger when the part of the finger is positioned within the container; and
    a removable sealing lid positioned along and against an edge of the wall portion to seal the opening and thereby provide storage for the sanitizing liquid within the container prior to use of the system for sanitizing,
    wherein, for first and second regions along the finger which are separated from one another by a distance, the first and second regions can simultaneously come into contact with different groups of bristles in the portable system
    wherein along a direction perpendicular to the central axis, the wall portion includes a taper between a relatively wide dimension along the opening and a relatively narrow dimension along the bottom portion and wherein the wall portion taper includes a curvature along the central axis.

2. The portable system of claim 1, where:
    the container height is sufficiently sized to enable the container to receive substantially the entire length of a finger, or the container height is in the range of 9 to 12 cm and an interior surface of the wall portion of the container is defined by the curve which is narrower at the bottom portion of the container and wider at the container opening,
    each in a plurality of the bristles has a height measurable along a direction in which the bristle extends away from an interior surface; and some in the plurality of the bristles vary in height, with bristles of different heights interspersed in a series or row of spaced apart bristles,
wherein the plurality of bristles creates a second curve that is defined by the heights of the bristles as they vary along the wall portion.

3. The portable system of claim 2 where:
the container is symmetric about the central axis with a variable outside diameter between the bottom portion and the opening; and
at least some of the bristles in the second group extend from the upper interior surface toward a central axis of symmetry; and
the outside diameter diminishes from a maximum outside diameter along the edge of the wall portion, to provide a relatively wide opening, to a minimum diameter near the bottom portion, with the interior diameter diminishing from the opening to the bottom portion.

4. The portable system of claim 1 where the edge of the wall portion is a sealing lip, and the removable sealing lid is bonded to the sealing lip to seal the opening.

5. The portable system of claim 4 where the sealing lid and the sealing lip are bonded together with an adhesive, or via a heating process or by welding.

6. A portable system, for cleaning or sanitizing a finger or a region about a fingernail, comprising:
a sealed container holding a sanitizing liquid, the container having an interior volume sized to receive a finger, with a horizontal bottom portion and a vertical wall portion for containing the liquid, the wall portion extending from the bottom portion to an opening along an edge of the wall portion through which a finger may be received into the container, the bottom portion having a horizontal orientation when positioned along a horizontal ground plane with the wall portion extending vertically above the ground plane along a central axis perpendicular to the ground plane,
the wall portion having opposing exterior and interior wall surfaces, the exterior wall surface facing away from the container interior, the majority of the interior wall surface extending along the exterior surface, and
the bottom portion having opposing exterior and interior bottom surfaces, the exterior bottom surface facing away from the container interior and the interior bottom surface facing the container interior, the container further comprising:
a plurality of rows of bristles, each row arranged in a series with each row of bristles adjacent another row of bristles,
wherein, with the wall portion extending vertically with respect to the bottom portion, a plurality of the rows of bristles inward from the wall portion interior surface of the container for contact with at least two spaced-apart portions of a finger inserted in the container, and each row of bristles along the vertically oriented wall portion contains a plurality of bristles that vary in size, with bristles of different heights interspersed in a series of spaced apart bristles within each row of bristles, and wherein:
when the finger is inserted within the container a first of the spaced-apart finger portion can contact bristles along the bottom portion while the second spaced-apart finger portion can simultaneously contact bristles along the wall portion, and
the wall portion extends a height from the bottom portion to an opening along an edge of the wall portion through which each of the fingers can be received into the container, the height of the container sufficient to enable the first finger to extend into the container from the finger tip to at least the second finger joint,
wherein along a direction perpendicular to the central axis, the wall portion includes a taper between a relatively wide dimension along the opening and a relatively narrow dimension along the bottom portion and wherein the wall portion taper includes a curvature along the central axis.

7. A sealed sanitizing system comprising a container and a sanitizing liquid stored therein, the container comprising a bottom and a wall portion extending along a first direction away from the bottom, parallel to a central axis, that contains the sanitizing liquid, the container including an interior surface along the wall portion and an interior surface along the bottom and a plurality of bristles having a varied pattern attached along the interior surface, the container having an elongate shape extending along the first direction and away from the bottom to define a cavity of depth suitable for receiving a finger, and dimensioned to permit a rubbing movement of the finger along the bristles in the first direction to facilitate sanitizing crevices along the finger with the liquid, the container bottom having a sufficiently flat exterior shape and size to enable the container to stand without additional support on a flat horizontal surface such as a table top, the wall portion including a sealable opening about an upper part of the wall portion where, when the bottom is positioned on the horizontal surface:
the container can occupy a vertically elongate, standing position above the horizontal surface with the wall portion extending upward, along the central axis, with respect to the horizontal surface;
with the container wall portion extending vertically above the horizontal surface, an interior dimension of the wall portion increases as a function of increase in vertical height along the container and above the bottom along the central axis;
the wall portion includes a taper between a relatively wide dimension along the sealable opening and a relatively narrow dimension along the bottom and wherein the wall portion taper includes a curvature along the central axis;
the wall portion includes a sealed cavity opening about the upper part of the wall portion, and
unsealing the cavity permits insertion of the finger to use the sanitizing liquid in combination with the varied pattern of bristles to sanitize along the crevices of the finger when the finger is rubbed along the bristles.

8. The sealed sanitizing system of claim 7 further including a removable seal positioned along and against an edge of the wall portion to seal the opening and keep liquid placed in the container prior to use of the system for cleaning or sanitizing, where the seal can be peeled away from the edge of the wall portion to unseal the opening and expose one or more patterns of bristles along at least one of the surfaces of the container.

9. The sealed sanitizing system of claim 7 where each of the plurality of bristles has a height measurable along a direction in which the bristle extends away from an interior surface, some of the bristles having an elongate height relative to bristle width or diameter with a ratio of height to width or height to diameter ranging from 37 to 125.

10. The sealed sanitizing system of claim 7 where the height of each in the plurality of bristles is measured along a direction in which the bristle extends away from an interior surface.

11. The sealed sanitizing system of claim 7 where the bristles are mixed in a pattern, allowing short and long bristles to simultaneously contact varied surface contours created by adjoining finger regions.

12. The sealed sanitizing system of claim 7 where the plurality of bristles includes a first plurality of bristles extending from the interior bottom surface for contact with a portion of a finger when positioned in the container and a second plurality of bristles extending from the interior surface and perpendicular to the container bottom so that the bristles-come into contact with a portion of a fingertip when positioned in the container.

13. The sealed sanitizing system of claim 7 where the plurality of bristles includes bristles extending from the interior wall surface that come into contact with liquid when liquid is in the container.

14. The sealed sanitizing system of claim 7 having a central axis, wherein portions of the finger further comprise a first portion of the finger located on a fingertip and a second portion of the finger spaced apart from the first portion of the finger located on an exterior surface of the finger about a length of the finger when the finger is inserted into the system.

15. The sealed sanitizing system of claim 14, wherein the interior dimension is a radial dimension extending from the central axis, the system having a height between the bottom and the sealed cavity opening that ranges from 5 cm to 12 cm.

16. The sealed sanitizing system of claim 15, further comprising an outer diameter of the sealed container which ranges from 2.5 cm to 3 cm.

17. The sealed sanitizing system of claim 16, wherein a ratio of the height and outer diameter ranges from 1.66:1 and 4.8:1.

18. The sealed sanitizing system of claim 16, wherein the outer diameter is a minimum at the bottom and a maximum at the sealed cavity opening.

19. The sealed sanitizing system of claim 7, where
(i) the container height is sufficient to enable the first finger to extend into the container from the tip of the finger to at least first and second joints of the finger, and
(ii) the varied bristles are arranged along the wall portion interior surface or along the bottom interior surface as a plurality of rows of bristles, each row arranged within a series of rows with each row of bristles adjacent another row of bristles, the rows of bristles extending within the cavity for contact with at least two spaced-apart portions of the finger when the finger is inserted in the cavity.

20. The sealed sanitizing system of claim 19, where
(i) the container height is sufficiently sized to enable the container to receive substantially the entire length of the finger, or the container height is in the range of 9 to 12 cm, and
(ii) when the container occupies a vertically elongate, standing position above the horizontal surface, with the bottom extending horizontally and the wall portion extending vertically upward with respect to the horizontal surface, each of multiple rows of bristles extends along the wall portion, each such row comprising bristles of both a first relatively tall height and bristles of a relatively short height such that in each of the multiple rows extending along the vertical wall portion a first relatively short bristle is positioned between at least first and second relatively tall bristles, a second relatively short bristle is positioned between at least third and fourth relatively tall bristles, and a fifth relatively tall bristle is positioned between at least a third and a fourth relatively short bristle.

21. The sealed sanitizing system of claim 19, where the rows of bristles are arranged so that when the finger is inserted within the container a first of the spaced-apart finger portions can contact bristles along the container bottom while the second spaced-apart finger portion can simultaneously contact bristles along the wall portion.

* * * * *